US010342902B2

(12) United States Patent
Bagwell et al.

(10) Patent No.: US 10,342,902 B2
(45) Date of Patent: Jul. 9, 2019

(54) DEVICE FOR IN SITU CLEARING OF OCCLUSIONS IN TUBING

(71) Applicant: Actuated Medical, Inc., Bellefonte, PA (US)

(72) Inventors: Roger B Bagwell, Bellefonte, PA (US); Ryan S Clement, State College, PA (US); Katherine M Erdley, Boalsburg, PA (US); Maureen L Mulvihill, Bellefonte, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 128 days.

(21) Appl. No.: 15/297,694

(22) Filed: Oct. 19, 2016

(65) Prior Publication Data

US 2017/0106128 A1 Apr. 20, 2017

Related U.S. Application Data

(60) Provisional application No. 62/243,458, filed on Oct. 19, 2015.

(51) Int. Cl.
*A61M 1/00* (2006.01)
*A61M 39/22* (2006.01)
(Continued)

(52) U.S. Cl.
CPC ........ *A61M 1/0064* (2013.01); *A61M 1/0084* (2013.01); *A61M 16/0402* (2014.02);
(Continued)

(58) Field of Classification Search
CPC ................ A61M 1/0064; A61M 39/22; A61M 16/0402; A61M 1/0078; A61M 1/0084;
(Continued)

(56) References Cited

U.S. PATENT DOCUMENTS 3,991,762 A 11/1976 Radford
4,638,539 A 1/1987 Palmer
(Continued)

FOREIGN PATENT DOCUMENTS

EP 1666168 A1 6/2006
JP 2005296092 10/2005
(Continued)

OTHER PUBLICATIONS

International Searching Authority; International Search Report and Written Opinion of the International Searching Authority; International Application No. PCT/US2013/064642; Patent Cooperation Treaty; pp. 1-11; publisher United States International Searching Authority; Published Alexandria, Virginia, United States of America; copyright and dated Jan. 16, 2014; (11 pages).

(Continued)

*Primary Examiner* — Rebecca E Eisenberg
(74) *Attorney, Agent, or Firm* — Metz Lewis Brodman Must O'Keefe LLC

(57) ABSTRACT

An occlusion clearing device and system for removing material from an artificial tube in situ includes a clearing stem having aspiration and irrigation conduits, where the irrigation conduit is disposed interior to, and terminates within the aspiration conduit. Material enters the clearing stem through aspiration, and irrigation is provided within the aspiration conduit to assist in aspiration through the clearing stem. A handset includes aspiration and irrigation tubing connecting to sources therefor, and further includes valves to control the flow through the tubing and conduits. These valves may be operated simultaneously with an actuator located on the handset, which may be done with one hand. A coupler at the operative end allows the clearing stem to gain access to the artificial tube for clearing while maintaining a closed system with a ventilator. Reciprocating (Continued)

motion may be generated and provided to the clearing stem to aid in occlusion removal.

44 Claims, 14 Drawing Sheets

(51) Int. Cl.
*A61M 16/04* (2006.01)
*A61M 25/00* (2006.01)

(52) U.S. Cl.
CPC ..... *A61M 39/22* (2013.01); *A61M 2025/0019* (2013.01); *A61M 2209/10* (2013.01)

(58) Field of Classification Search
CPC ...... A61M 2025/0019; A61M 2209/10; A61M 16/04; A61M 16/0463; A61B 90/70; A61B 2090/701; A61B 1/00068
See application file for complete search history.

(56) References Cited

U.S. PATENT DOCUMENTS

| | | | |
|---|---|---|---|
| 4,696,296 A | 9/1987 | Palmer | |
| 4,979,939 A | 12/1990 | Shiber | |
| 5,003,657 A | 4/1991 | Boiteau | |
| 5,029,580 A | 7/1991 | Radford et al. | |
| 5,181,908 A | 1/1993 | Bell | |
| 5,197,949 A * | 3/1993 | Angsupanich | A61B 17/320708 600/571 |
| 5,220,916 A | 6/1993 | Russo | |
| 5,251,356 A | 10/1993 | Oaki et al. | |
| 5,254,098 A | 10/1993 | Ulrich et al. | |
| 5,277,177 A | 1/1994 | Page et al. | |
| 5,279,549 A | 1/1994 | Ranford | |
| 5,897,534 A | 4/1999 | Heim et al. | |
| 5,902,314 A | 5/1999 | Koch | |
| 5,908,403 A | 6/1999 | Bosma et al. | |
| 6,047,431 A | 4/2000 | Canonica | |
| 6,082,361 A | 7/2000 | Morejon | |
| 6,575,944 B1 | 6/2003 | McNary | |
| 6,725,492 B2 | 4/2004 | Moore | |
| 7,051,737 B2 | 5/2006 | Kolobow et al. | |
| 7,478,636 B2 | 1/2009 | Madsen et al. | |
| 7,581,541 B2 | 9/2009 | Madsen et al. | |
| 7,918,870 B2 | 4/2011 | Kugler et al. | |
| 7,938,819 B2 | 5/2011 | Kugler et al. | |
| 8,025,665 B2 | 9/2011 | Kugler et al. | |
| 8,083,727 B2 | 12/2011 | Kugler et al. | |
| 8,157,919 B2 | 4/2012 | Vazales et al. | |
| 8,381,345 B2 | 2/2013 | Vazales et al. | |
| 8,382,908 B2 | 2/2013 | Vazales et al. | |
| 8,458,844 B2 | 6/2013 | Vazales et al. | |
| 8,468,637 B2 | 6/2013 | Vazales et al. | |
| 8,534,287 B2 | 9/2013 | Vazales et al. | |
| 8,601,633 B2 | 12/2013 | Vazales et al. | |
| 9,095,286 B2 | 8/2015 | Vazales et al. | |
| 2002/0069893 A1 | 6/2002 | Kawazoe | |
| 2002/0099387 A1 | 7/2002 | Gauderer et al. | |
| 2003/0181876 A1 | 9/2003 | Ahn et al. | |
| 2003/0181934 A1 | 9/2003 | Johnston et al. | |
| 2003/0209258 A1 | 11/2003 | Morejon | |
| 2004/0181194 A1 | 9/2004 | Perkins | |
| 2006/0276743 A1 | 12/2006 | MacMahon et al. | |
| 2007/0038158 A1 | 2/2007 | Nita | |
| 2007/0093779 A1 | 4/2007 | Kugler et al. | |
| 2007/0093780 A1 | 4/2007 | Kugler et al. | |
| 2007/0093781 A1 | 4/2007 | Kugler et al. | |
| 2007/0093782 A1 | 4/2007 | Kugler et al. | |
| 2007/0093783 A1 | 4/2007 | Kugler et al. | |
| 2007/0225615 A1 | 9/2007 | Chechelski et al. | |
| 2007/0244423 A1 | 10/2007 | Zumeris et al. | |
| 2008/0200877 A1 | 8/2008 | Panotopoulos | |
| 2009/0188531 A1 | 7/2009 | Boyle | |
| 2009/0264833 A1 | 10/2009 | Boyle | |
| 2009/0270800 A1 | 10/2009 | Spurchise et al. | |
| 2011/0106019 A1 | 5/2011 | Bagwell et al. | |
| 2011/0276079 A1 | 11/2011 | Kugler et al. | |
| 2012/0016272 A1 | 1/2012 | Nita et al. | |
| 2012/0071854 A1 | 3/2012 | Kugler et al. | |
| 2012/0136382 A1 | 5/2012 | Kugler et al. | |
| 2014/0102445 A1 * | 4/2014 | Clement | A61M 25/00 128/202.13 |
| 2014/0207056 A1 | 7/2014 | Bono et al. | |
| 2016/0038660 A1 * | 2/2016 | Loebl | A61M 1/0064 604/28 |

FOREIGN PATENT DOCUMENTS

| | | |
|---|---|---|
| WO | WO2004098654 A2 | 11/2004 |
| WO | WO2007033052 | 3/2007 |
| WO | WO2011126812 A1 | 10/2011 |

OTHER PUBLICATIONS

United States Patent and Trademark Office; Office Action Summary; U.S. Appl. No. 14/182,088; dated Sep. 11, 2014; pp. 1-17; publisher United States Patent and Trademark Office, Alexandria, Virginia; USA; copyright and dated Sep. 11, 2014; (17 pages).

International Searching Authority; International Search Report and Written Opinion of the International Searching Authority; International Application No. PCT/US16/57693; Patent Cooperation Treaty; pp. 1-19; publisher United States International Searching Authority; Published Alexandria, Virginia, US; copyright and dated Jan. 12, 2017; copy enclosed (19 pages).

* cited by examiner

DEVICE FOR IN SITU CLEARING OF OCCLUSIONS IN TUBING

CROSS-REFERENCE TO RELATED APPLICATIONS

The present application claims the benefit of U.S. Provisional Application Ser. No. 62/243,458, filed on Oct. 19, 2015, the contents of which are incorporated herein by reference in their entirety.

STATEMENT REGARDING FEDERALLY SPONSORED RESEARCH OR DEVELOPMENT

This invention was made with government support under HD074310 awarded by the National Institutes of Health, and 0810029 and 0923861 awarded by the National Science Foundation. The government has certain rights in the invention.

FIELD OF THE INVENTION

The present invention pertains generally to the field of medical devices, and more specifically to a system for in-situ clearing of occlusive material such as secretions in endotracheal tubes and other tubes in the body where secretions or other materials accumulate and negatively impact tube patency.

BACKGROUND

The following is a description of the background of endotracheal tubes (ETTs). It should be understood that the device and method of the present invention is not limited to the clearing of ETTs but is applicable to a range of artificial tubes such as indwelling catheters, pigtail catheters, abscess drains, and chest tubes and that ETTs are being discussed simply by way of example. It should also be understood that the device and method of the present invention is not limited to secretions but is applicable to a range of accumulating and/or occluding materials such as blood, clots, and ingrown tissues/membranes.

Automated mechanical ventilation is often required for patients under anesthesia and for longer-term breathing assistance in compromised patients. Endotracheal tubes are placed in the upper respiratory tract of patients to provide direct airway access when connected to a mechanical ventilator. Annually, 50 million ETTs are sold globally. Patients intubated with ETTs are unable to effectively clear lung secretions, and therefore secretions can accumulate and partially occlude the inside of the ETT. This leads to increased airway resistance and a potentially negative impact on patient health if not remedied. Without proper air humidification, the secretions also potentially become dried, thick, and difficult to remove.

The most routine method to maintain ETT patency is periodic aspiration with a suction catheter. The suction catheter is designed to be momentarily inserted down the ETT manually while attached to a negative pressure source. There are two general types of suction catheters: open and closed. An open suction catheter requires the patient to be disconnected from the ventilator for the suctioning procedure. A closed suction catheter is enclosed in a protective sleeve and remains attached to the ventilator circuit the entire time. Suctioning can occur without having to shut off the ventilator or disconnect the patient, because there is a diaphragm that maintains an air-tight seal around the suctioning catheter. Whether open or closed, the general suction procedure remains the same. With one hand stabilizing the proximal end of the ETT, the suction catheter is fed into the ETT with the opposite hand until the end is reached, being careful to not over-insert the catheter beyond the tip of the ETT. While retracting the suction catheter, a valve is pressed enabling the negative pressure source to apply a vacuum to the inner lumen of the suction catheter to aspirate out secretions accumulated on the inner wall of the ETT. It is generally desired for the entire suction procedure to be performed in 10-15 seconds, or 5 seconds in children to minimize the impact of the suctioning procedure on lung mechanics and respiration. Generally, a patient will require suctioning every 4-6 hours, but the process may be performed with greater regularity if necessary. The procedure is recommended on an as needed basis, not a regular interval, due to the detrimental effect on the patient.

Attempts to clear the ETT using standard techniques are often ineffective, time consuming, expensive, and an agonizing experience for the patients, families, and health care providers. Standard methods can also dislodge bacteria containing particles into the lungs. Ventilator Acquired Pneumonia (VAP) is a major source of infection in hospitals, and is often due to the direct path to the lungs for bacteria from ETT intubation. Standard suctioning has an effect on lung mechanics, including decreased tidal volume and lung compliance. Clinical side effects include hypoxia (low oxygen in blood), bradycardia (low heart rate), or atelectasis (collapse of part of the lung). In general, the long term effects of acute changes in lung mechanics or cumulative exposures to short term clinical side effects of suctioning on long term respiratory health is not known. Still, minimizing the potential negative impacts of the suctioning process on the lungs is desirable.

Negative effects can be minimized with use of smaller diameter suction catheters, which allow improved airflow during the insertion of the catheter and when actively suctioning. Guidelines suggest choosing a suction catheter whose outer diameter is less than half the inner diameter of the ETT. However, with narrow ETTs (such as neo-natal or pediatric patients) this is difficult to achieve without severely limiting secretion aspiration effectiveness using standard methods. Such small diameter suction catheters may easily clog, depending on the consistency of the secretions. In addition to airflow considerations, larger suction catheters may be difficult to insert if the catheter diameter to ETT inner diameter ratio is larger than 0.7.

While the practice is now largely discouraged, occasionally physiologic saline may be first instilled at the inlet to the ETT in an attempt to hydrate and thin the secretions to encourage its removal during the subsequent suctioning procedure. Additional goals of saline instillation may include lubricating and easing the insertion of the catheter itself, and/or elicitation of a cough from the patient to aid secretion removal. The current methods of instilling saline into ETTs are not precise and there is risk of excess fluid entering the lungs and possibly causing dispersion of adherent contaminating material. Reports further suggest saline instillation may cause greater blood oxygen desaturation than suctioning without saline. Despite lack of evidence supporting saline instillation and its potential risks, some clinicians continue the practice.

When suctioning is unable to restore patency quickly, the only recourse is to replace the ETT, further raising the risk of VAP while also depriving the patient of oxygen until the patient is re-intubated and reconnected to the ventilator. In addition, the re-intubation process itself can agitate the patient's airway and lead to inflammation and/or injury.

There remains a need to safely and quickly clear ETTs, while reducing the negative impact the suction procedure has on the lung mechanics of an already compromised patient.

SUMMARY OF THE INVENTION

The present invention is directed to an occlusion clearing device and system that may be used to clear secretions from ETTs and other tubes in the body more quickly, thoroughly, and with less impact on the patient's lungs or other organs than any current method. The device may operate within a closed system, meaning that the connection to and function of the ventilator is not interrupted when secretion clearing is conducted. Gentle oscillation motion may be applied to assist in the clearing of the secretions or other material.

The occlusion clearing device includes a clearing stem having an aspiration conduit and an irrigation conduit within the aspiration conduit. This dual lumen stem allows distal delivery of low volume, continuous irrigation balanced with aspiration, allowing secretions to be broken up and aspirated. Notably, the irrigation conduit terminates inside the aspiration conduit, and si spaced a distance from the terminal end of the aspiration conduit, such that substantially all of the irrigation fluid provided to the operative end of the clearing stem remains within the clearing stem and is aspirated back up the clearing stem through the aspiration conduit. Therefore, contact of fluid or debris with the endotracheal tube is avoided. A coupler may be used to connect the endotracheal tube to the device, so that the operative distal end of the clearing stem can be moved into the tube for clearing occlusive material. This coupler may also include a port for the ventilator to attach, so that ventilation can continue throughout the process of occlusion clearing. The device also includes a handset having aspiration and irrigation tubing that connects to respective sources, and valves for each to control the aspiration and irrigation flow, respectively.

These valves may be activated simultaneously with an actuator, which may also be locked in position to keep the aspiration and irrigation on or off. Reciprocating motion, such as vibration, although not necessary, may also aid the break-up and aspiration of thicker secretions, allow easier insertion (less hang up in tube), and to prevent secretions from getting stuck in the aspiration conduit. Implementing the motion applied to the clearing stem, along with the irrigation and aspiration, while maintaining the closed system, may require the use of custom connections.

The occlusion clearing device, together with its particular features and advantages, will become more apparent from the following detailed description and with reference to the appended drawings.

DETAILED DESCRIPTION

Figure 1:
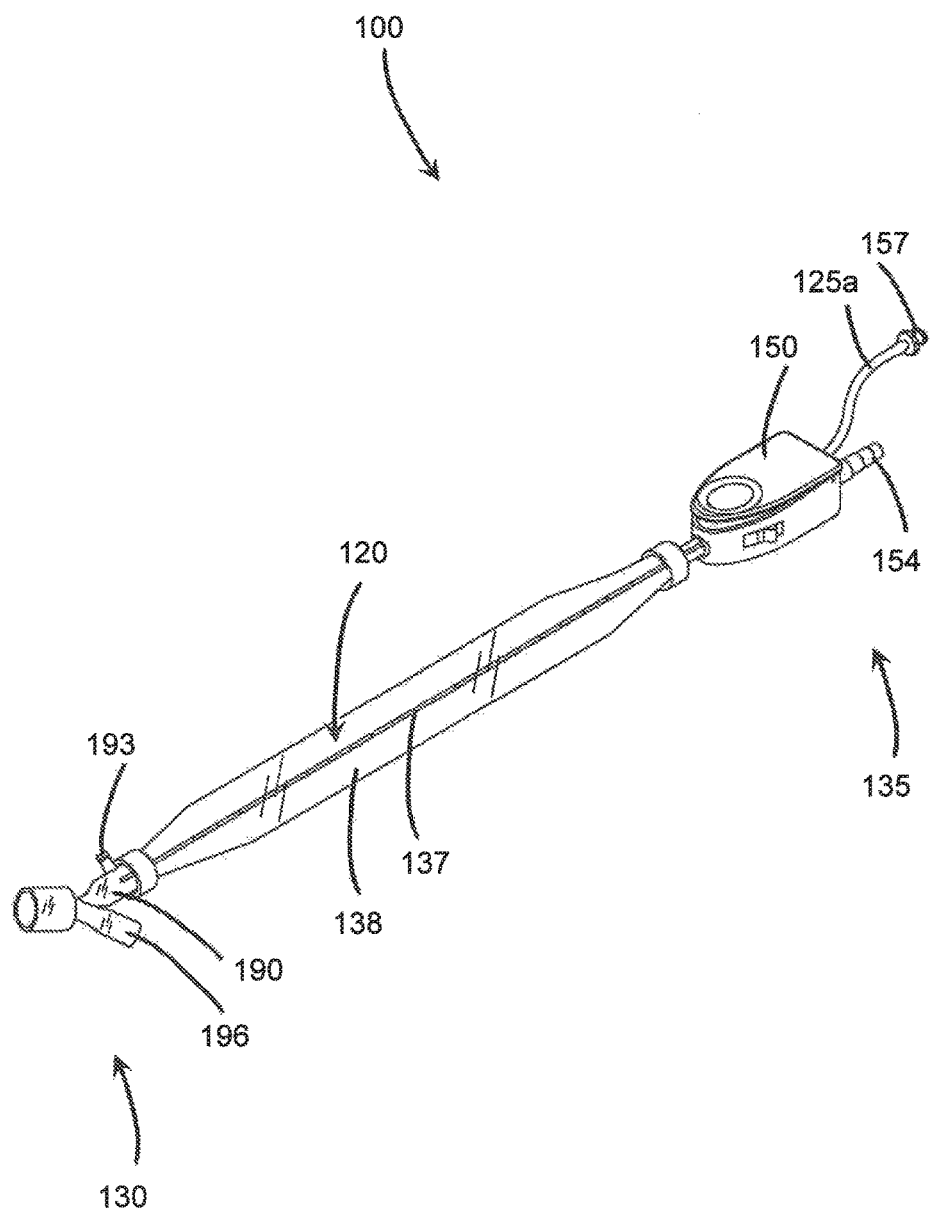
FIG. 1 is a perspective view of one embodiment of the occlusive clearing device.

It is hereby noted that the term "in situ" is defined as performing an act on an element while the element is being utilized for its commonly known function. For example, performing the act of clearing fluids or material from an ETT in situ refers to the fluids or material in an ETT while the tube is dwelling within the trachea or respiratory system of a living being, human or other.

As shown in the accompanying drawings, the present invention is directed to an occlusion clearing device which employs several features that, individually and together, enhance aspiration effectiveness while occupying less cross-sectional area compared to existing devices on the market. The need to occupy less cross-sectional area, while remaining similarly or more effective than existing devices is important, but particularly so in small diameter tubes, such as neonatal ETTs with outer diameters less than or equal to 4 mm, for reason mentioned above.

The features of the present invention are aimed primarily at maintaining and improving flow of occlusive material (e.g. secretions, mucus, blood) within the aspiration lumen, which is highly prone to blockage due to the small cross-sectional area. An irrigation lumen is disposed within and runs parallel to the aspiration lumen, and terminates within the aspiration lumen before the clearing stem ends. The irrigation fluid (e.g. saline) sent to the distal end stays entirely within the clearing stem and does not exit into the tube to be cleared. Thus, the irrigation fluid helps lubricate the occlusive material once it is in the aspiration lumen and reduce viscosity of the material, which keeps the occlusive material from clogging the aspiration lumen during removal. In addition, the occlusion clearing device includes a coupler that permits access of the clearing stem to the tube having the occlusion to be cleared while still maintaining a closed system, such that the subject can remain on ventilation while the tube is being cleared.

In some embodiments, vibration may be delivered to the clearing stem of the device to assist in breaking up the occlusive material in the tube being cleared at the distal end, and also providing gentle agitation with irrigation fluid to keep the occlusive material moving during aspiration. The vibration may also reduce interfacial friction between the clearing stem and the inner side of the tube being cleared, making the clearing stem easier to insert, which may be performed with just a single hand.

As used herein, the terms "occlusion," "secretion," and "clog" may be used interchangeably, and refer to occlusive material in a tube disposed within a living subject, such as a patient. The subject may be a human or any other animal. The tube may be any artificial or natural tube disposed within a subject, and may be resident within the subject for a period of time. For instance, such tubes may include, but are not limited to endotracheal and tracheostomy tubes. Such tube is to be cleared when it has acquired material which is desired to be removed, such as foreign material or an amount of material (foreign or natural, such as secretions, mucus, and build-up of medication) that impairs the function of the tube, creates an unhygienic or uncomfortable situation for the subject, or may otherwise be medically necessary or preferable to remove. Such material is referred to herein as "occlusive material." Accordingly, occlusive material need not fully block or close off the tube to be cleared, but may refer to any material within the tube that is desired to be removed.

With reference now to the Figures, FIG. 1 shows one embodiment of the occlusion clearing device 100 of the present invention. The device 100 includes a clearing stem 120 having an operative distal end 130 on one end, and a proximal end 135 on the opposite end. The distal end 130 of the clearing stem 120 may be fed into the tube to be cleared (not shown), such as through a coupler 190, in order to reach the occlusion for removal. The clearing stem 120 may include depth markings 137 that aid the user during insertion into the tube to be cleared, to ensure the clearing stem 120 is not inserted beyond the end of the tube.

The clearing stem 120 is made up of an aspiration conduit 121 having an aspiration lumen 122 defined there through, and an irrigation conduit 125 disposed within the aspiration conduit 121. During use, occlusive material is pulled into the aspiration conduit 121 of the clearing stem 120 at the distal end 130, and irrigant from the irrigation conduit 125 keeps the occlusive material sufficiently softened that it continues to move proximally through the clearing stem 120 for removal and does not clog the clearing stem 120. At the proximal end 135, the device 100 includes a handset 150 housing aspiration tubing 121a and irrigation tubing 125a. The aspiration tubing 121a carries the aspiration out of the device through an aspiration port 154. The irrigation tubing 125a carries irrigation into the device from an irrigation port 157. The handset 150 also includes valves controlling the flow of aspiration and irrigation through the respective tubing 121a, 125a, and consequently also controls the flow rate in the clearing stem 120. Accordingly, the handset 150 is intended to be gripped by a clinician or other user for maneuvering and actuation of the device 100 for aspiration of occlusive material from the tube to be cleared.

In at least one embodiment, a protective sleeve 138 may cover the clearing stem 120 and prevent it from being contaminated by the environment. For example, the protective sleeve 138 may maintain a sterile environment for the clearing stem 120 once the device 100 is sterilized. At a minimum, the protective sleeve 138 prevents a user from directly touching the clearing stem 120, and protects it from dirt and debris that may be in the air. The protective sleeve 138 may connect at one end to the coupler 190 and at the other end to the handset 150, such as at an adapter 153, so that the protective sleeve 138 spans the entire length of the clearing stem 120 between each of these components.

Figure 2:
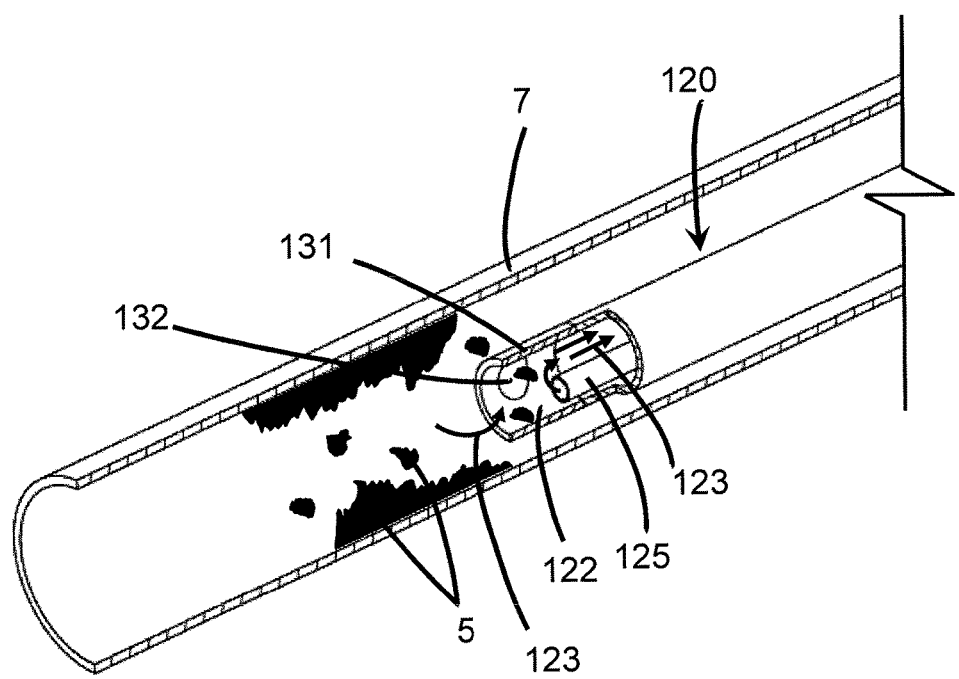
FIG. 2 is a partial cutaway of the distal end of the clearing stem, positioned in an artificial tube having occlusive material being removed through the clearing stem.

As shown in FIG. 2, the distal end of the clearing stem 120 is operative to withdraw occlusive material 5 from a tube 7. The occlusive material 5 may include but is not limited to secretions, mucus, phlegm, blood, etc. In use, the distal end 130, and specifically the distal tip 131, of the aspiration conduit 121 is positioned in close proximity to the occlusive material 5 that is to be removed from the tube 7. Aspiration is applied to draw the occlusive material 5 into the aspiration lumen 122, and is removed from the tube 7 by being pulled in an aspirational flow direction 128 away from the distal end 130 of the device 100.

As is depicted throughout FIGS. 2-4B, the aspiration conduit 121 includes at least one opening 132 in the distal tip 131. In at least one embodiment, the distal tip 131 includes an opening at the terminal end of the aspiration conduit 121. In some embodiments, as shown in FIGS. 3A and 4A, the distal tip 131 includes a plurality of openings 132 in the aspiration conduit 121. Any number and placement of openings 132 is contemplated herein. For instance, one of these openings 132 may be located at the terminal end of the aspiration conduit 121, and at least one additional opening 132 may be formed in the wall of the aspiration conduit 121 at the distal tip 131 spaced away from the terminal end of the distal tip 131. FIG. 3A shows two openings 132 directly opposite each other across the diameter of the aspiration conduit 121. The number and placement of these openings may vary in order to optimize the removal of occlusive material. For instance, two openings 132 may be present and may be set back or proximal from the terminal end of the distal tip 135 by the same distance or different distances, such that the opening on one side is closer to the distal tip of the aspiration conduit 121 than the other opening. Typically the most distal edge of the most distal openings 132 will be a preselected distance from the terminal end, such as at least approximately one-half diameter (one radius) back from the terminal end of the distal tip 135 of the aspiration conduit 121 or farther. For instance, the openings 132 shown in FIG. 3A for an aspiration conduit 121 having an internal diameter 0.036 inches may be spaced back from the terminal end by a distance in the range of 0.009 to 0.100 inches, and may be in the range of 0.012 to 0.050 inches, and may preferably be 0.015 inches. The openings 132 shown in FIG. 3A for an aspiration conduit 121 having and internal diameter 0.057 inches may be spaced back from the terminal end by a distance in the range of 0.012 to 0.125 inches, and may be in the range of 0.018 to 0.060 inches, and may preferably be 0.025 inches.

Figure 3A:
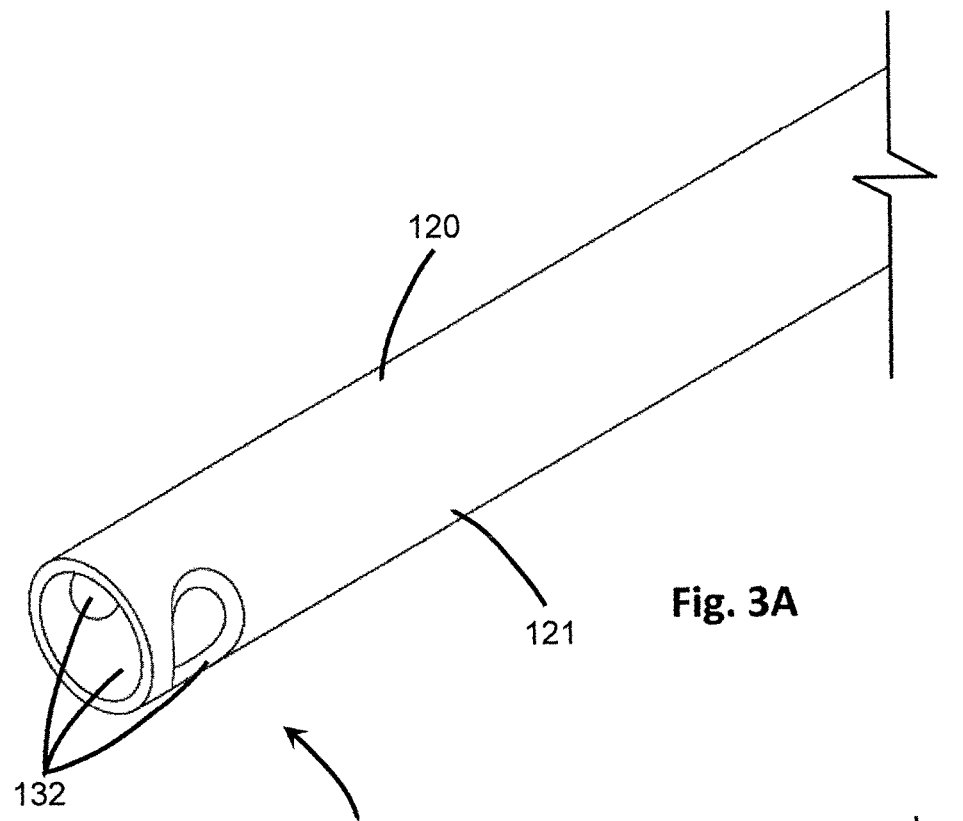
FIG. 3A is a perspective view of one embodiment of the distal end of the clearing stem.

The opening(s) 132 are dimensioned to permit occlusive material 5 to pass there through, and may be any size and shape as permits passage of occlusive material 5. For instance, in at least one embodiment as shown in FIGS. 2-4B, the opening(s) 132 are circular. Typical diameters for circular openings 132, such as shown in FIG. 3A, for an aspiration conduit 121 having an internal diameter 0.036 inches (such as used to clear a 2.5 mm tube) may be in the range of 0.018 to 0.045 inches, or more preferably 0.025 to 0.036 inches, and may be 0.030 inches. Typical diameters for circular openings 132 such as shown in FIG. 3A for an aspiration conduit 121 having an internal diameter of 0.057 inches (such as used to clear a 3.5 mm tube) may be in the range of 0.025 to 0.067 inches, or more preferably 0.030 to 0.060 inches, and may be 0.050 inches. In at least one other embodiment, the terminal opening 132 may be circular and additional openings 132 at the distal tip 131 may be oval or oblong in shape, and may have a longer dimension either parallel to the length of the aspiration conduit 121 or in the direction of the circumference of the aspiration conduit 121. For instance, openings 132 in the aspiration conduit 121 may be oval in shape and have a longer dimension perpendicular to the length of the aspiration conduit 121, in the direction of the circumference of the aspiration conduit 121, so as to increase the area for receiving the occlusive material 5 into the aspiration lumen 122. Regarding size, the opening(s) 132 are generally approximately the same diameter or smaller than the diameter of the aspiration lumen 122. These are only examples provided for illustrative purposes, and should not be considered limiting.

The occlusive material 5 is sucked into the clearing stem 120, specifically the aspiration lumen 122, and aspirated back towards the proximal end of the device as shown by the aspirational flow arrows 123. Suction pressure is applied at the proximal end of the device 100 to establish aspirational flow 123, and may be between 50 and 200 mm Hg. In at least one embodiment, the aspiration pressure that drives aspiration flow 123 is preferably between 60 and 150 mm Hg. In still further embodiments, the aspirational pressure is between 80-130 mm Hg, and may preferably be 120 mm Hg. Greater and lower aspirational pressures and resulting flow rates are also possible and contemplated herein.

The size or diameter of the clearing stem 120, and specifically the aspiration conduit 121, will vary, but is small enough to be inserted into a tube 7 to be cleared, such as an endotracheal tube (ETT) or tracheostomy tube, although any tube 7 having occlusive material 5 in need of removal is contemplated. Therefore, the aspiration conduit 121 is also large enough to accommodate occlusive material 5 therein as it is aspirated away. The wall of the aspiration conduit 121 is sufficiently thick to provide structure for the clearing stem 120 and will not collapse under the aspirational pressure when applied, and yet is thin enough to be navigated through the tube 7 to reach the occlusive material 5 for clearing. For example, for a 2.5 mm ETT, one embodiment of the aspiration conduit 121 has an internal diameter of 0.030 to 0.057 inches. This internal diameter corresponds to the diameter of the aspiration lumen 122. In other embodiments, the internal diameter is in the range of 0.035 to 0.045 inches, and may preferably be 0.036 inches in some embodiments. The wall thickness of the aspiration conduit 121 may be altered to affect the stiffness, ability to withstand higher suction pressures, or to adjust the outside diameter of the aspiration conduit. For example, typically wall thicknesses for the aspiration conduit 121 may be in the range of 0.002 to 0.012 inches in some embodiments. In certain embodiments, the wall thickness of the aspiration conduit 121 may be in the range of 0.004 to 0.010, more preferably may be 0.006 inches in certain embodiments.

In examples where a 3.5 mm ETT is to be cleared, the aspiration conduit 121 may have an internal diameter of 0.045 to 0.080 inches. In some embodiments, the internal diameter is the range of 0.055 to 0.070 inches, and may preferably be 0.057 inches. The wall thickness of the aspiration conduit 121 may be in the range of 0.002 to 0.012 inches. In some embodiments, the wall thickness may be in the range of 0.004 to 0.010 inches, and may more preferably be 0.006 inches in some embodiments. Of course, smaller and larger wall thicknesses and lumen diameters are also contemplated herein, depending on the size of the tube 7 to be cleared and the type, character and amount of occlusive material 5 to be removed.

Figure 3B:
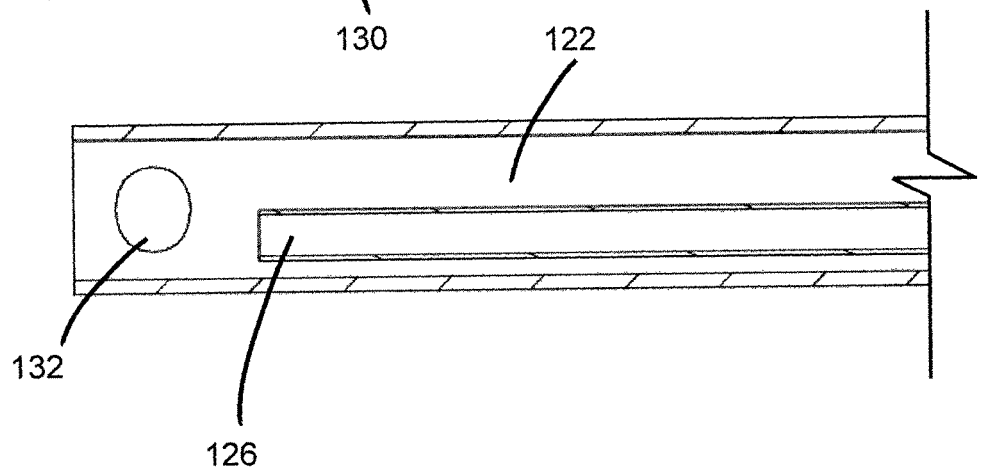
FIG. 3B is a cross-section of the distal end of the clearing stem of FIG. 3A.
Figure 4A:
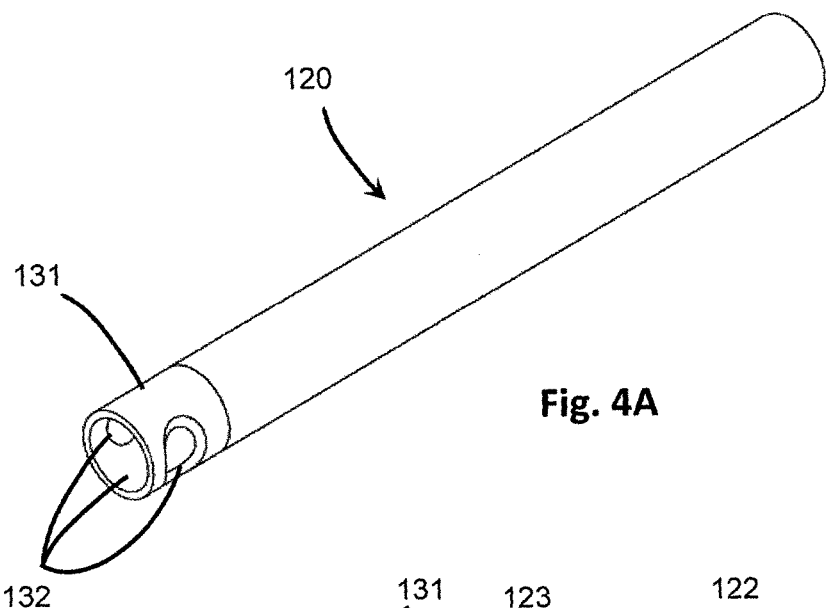
FIG. 4A is a perspective view of another embodiment of the distal end of the clearing stem.
Figure 4B:
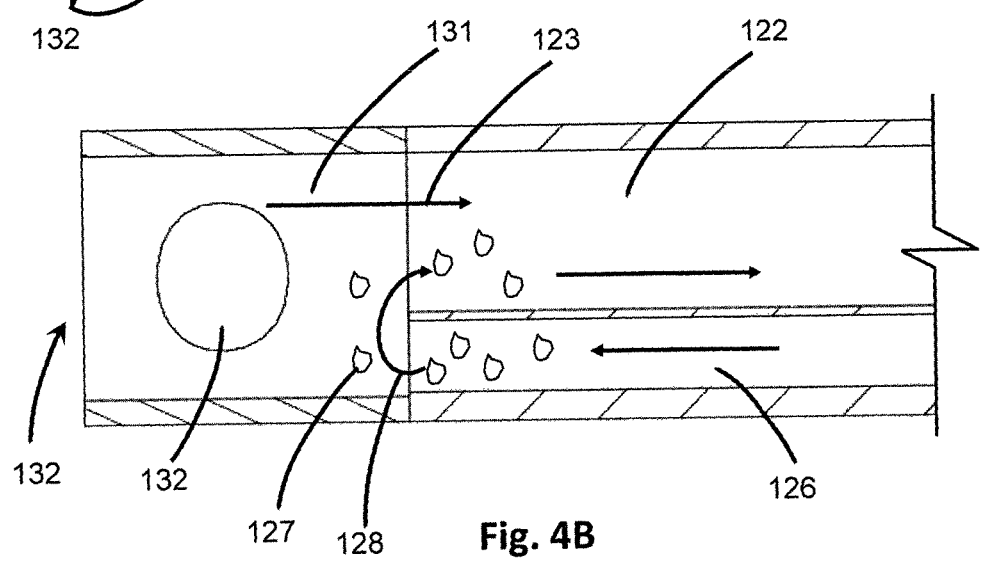
FIG. 4B is a cross-section of the distal end of the clearing stem of FIG. 4A.

As depicted in FIGS. 2-4B, the clearing stem 120 also includes an irrigation conduit 125 having an irrigation lumen 126 therein. The irrigation conduit 125 is at least partially disposed within the aspiration lumen 122 of the clearing stem 120, and provides irrigant 127 to the distal end of the clearing stem 120. The irrigation conduit 125 ends within the aspiration lumen 122, such that the irrigation conduit 125 is entirely within the aspiration lumen 122 at the distal end 130 of the clearing stem 120. As occlusive material 5 is drawn into the clearing stem 120 through the opening(s) 132, it mixes with irrigant 127 being gently expelled from the irrigation lumen 126 into the aspiration lumen 122, as best shown in FIGS. 2 and 4B. This mixing of irrigant 127 and the occlusive material 5 helps to lubricate the occlusive material 5 within the device 100 and prevent it from clogging the aspiration lumen 122, and therefore maintain the patency of the clearing stem 120. As most clearly shown in FIGS. 3B and 4B, the irrigation conduit 125 terminates within the aspiration lumen 122 before, or proximal to, the opening(s) 132 at the distal tip 131. This retracted position allows the irrigant 127 to exit the irrigation lumen 126 and mix with occlusive material 5 while remaining entirely within the clearing stem 120. In other words, the positioning of the irrigation conduit 125 within the aspiration lumen 122 prevents irrigant 127 from leaking out of or exiting the clearing stem 120 through the opening(s) 132. This is particularly important in cases where the tube 7 being cleared is an ETT or tracheostomy tube residing in the subject patient's respiratory tract, where further fluid added to the tube, and potentially the patient's lungs or airway, should be avoided.

Both the internal diameter of the irrigation conduit 125 (the diameter of the irrigation lumen 126) and the delivery pressure of irrigant 127 provided at the proximal end of the device 100 affect irrigant flow rate to the distal end of irrigation conduit 125. The irrigant flow rate through the irrigation lumen 126 is coordinated with aspiration flow though the aspiration lumen 122 to ensure that no irrigant 127 exits the openings 132 in the distal end 130 of the clearing stem 120. The irrigation lumen 126 may have a diameter in the range of 0.005 to 0.015 inches in some embodiments. In other embodiments, it may be in the range of 0.008 to 0.013 inches, and may preferably be about 0.010 inches. These are but a few preferred diameters, and other diameters larger and smaller are also contemplated. The irrigation lumen 126 diameter may depend on the size of the aspiration lumen 122 into which the irrigation conduit 125 is placed.

The irrigation conduit 125 may have different wall thicknesses depending on the desired stiffness, ability to withstand higher irrigant pressures, or based on the diameter of the aspiration conduit 121, which may alter the size of the aspiration lumen 122 and aspirant flow rate. For instance, in some embodiments, the irrigation conduit 125 may have a wall thickness in the range of 0.0005 to 0.0030 inches. In some embodiments, the wall thickness is in the range of 0.0008 to 0.0015 inches, and may preferably be 0.0010 inches.

The delivery pressure of irrigant 127 may vary, such as from 1 psi to 20 psi. In some embodiments, the irrigation pressure may be from 2 psi to 15 psi. In still other embodiments, the irrigation pressure may be from 6 psi to 10 psi, and may preferably be 7 psi. Irrigant flow rates may vary, such as from 0.003 g/sec to 0.100 g/sec in some embodiments. In certain embodiments, the irrigant flow rate may be from 0.010 g/sec to 0.050 g/sec. In still other embodiments, it may be from 0.015 g/sec to 0.035 g/sec, and may preferably be 0.025 g/sec.

The physical dimensions of the aspiration conduit 121 and irrigation conduit 125 can be altered to affect the aspiration flow 123 and irrigant flow 128, respectively. If the delivery pressure of irrigant 127 and the aspiration pressure are fixed and unchanging, increasing the diameter of the irrigation lumen 126 will increases the irrigant flow 128 relative to the aspiration flow 123. Likewise, decreasing the diameter of the irrigation lumen 126 will decrease the irrigant flow 128 relative to the aspiration flow 123. The wall thicknesses of the irrigation conduit 125 and aspiration conduit 121 can also affect the relative flows. As an example, if the aspiration conduit 121 inner diameter and irrigant conduit 125 outer diameter remain fixed, increasing the irrigant conduit 125 wall thickness will necessarily reduce the available area in the irrigant lumen 126, thereby reducing the irrigant flow 128.

Both the irrigation conduit 125 and the aspiration conduit 121 may be made of polymeric materials typically used for medical catheter applications including, but not limited to, polyurethane, polyvinylchoride, polyimide, and polyamide including copolymers and blends that can be utilized to adjust the physical properties to balance strength, stiffness, hardness, etc. Additionally, the materials, dimensions or both maybe altered along the length of the clearing stem 120 from the distal end 130 to proximal end 135 to provide a balance of strength, stiffness, hardness, and other factors as may be beneficial at different portions of the clearing stem 120. Reinforcements may be utilized to alter these properties. Such reinforcements may include additives to the polymeric material, such as glass fiber or spiral and braided wire reinforcement.

In some embodiments, the clearing stem 120 may have variable stiffness along its length. For instance, a stiffer material may be used at the proximal end 135 for maximum aspiration lumen 122 diameter while maintaining or improving pushability. The distal end 130, however, may be flexible to prevent tissue damage if contact with biological surfaces occurs. In some embodiments as in FIGS. 4A and 4B, the distal tip 131 may be made of a different material than the rest of the clearing stem 120. For instance, the distal tip 131 may be made of a softer or more flexible material than the rest of the clearing stem 120. This allows for a more rigid material to be used throughout most of the length of the clearing stem 120 to maximize the pushability of the clearing stem 120 as it is being inserted into the tube 7 and a more flexible material to be used at the distal tip 131 to ensure tissue damage is minimized in the event that the clearing stem 120 is inadvertently over inserted. Examples of a softer material for use in the distal tip 131 may include materials having a Shore hardness or durometer in the range of 30 A to 100 A (60 D), where "A" refers to the Shore A scale and "D" refers to the Shore D scale, which partially overlap. In some embodiments, the softer distal tip 131 material may be in the range of 70 A (12 D) to 90 A (45 D). In certain embodiments, it may be about 82 A (35 D). In contrast, the more rigid material used for the proximal end 135 of the clearing stem 120 may be in the range of 80 A (32 D) to 90 D. In some embodiments, the more rigid material may be in the range of 95 A (50 D) to 80 D, and may preferably be 72 D. The particular materials used for either the softer or more rigid sections of the clearing stem 120 may be polymeric materials and blends as are commonly used in medical grade catheters, although any material suitable for medical use may be used. These are illustrative examples, and are not intended to be limiting.

The irrigation conduit 125 and aspiration conduit 121 may be separate components, as shown in FIG. 3B. In other embodiments, as in FIG. 4B, the irrigation conduit 125 and aspiration conduit 121 may be integrally formed, such as made from a single multi-lumen extrusion. In still other embodiments, the irrigation conduit 125 and aspiration conduit 121 may be formed separately, but may be secured to one another in the device 100. The multi-lumen extrusion can be a more rigid material, as previously discussed, and the distal tip 131 can be a more compliant material bonded to the end of the extrusion. This configuration allows the irrigation lumen 126 to be set back from the terminal end of the clearing stem 120 so that substantially all of the irrigant 127 that exits the irrigation lumen 126 is aspirated back in the aspiration flow 123 direction to the proximal end of the occlusion clearing device 100 before it can exit the openings 132.

Figure 5A:
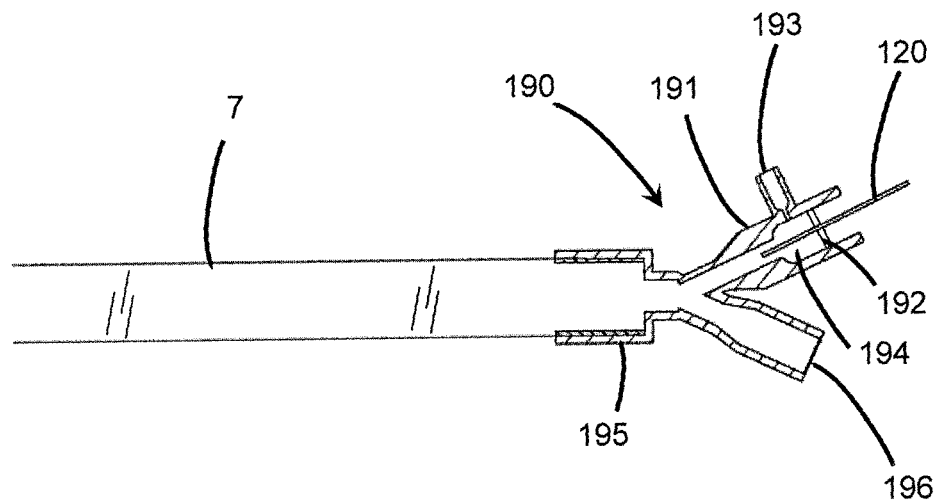
FIG. 5A is a partial cross-section of a coupler connected to an endotracheal tube, in which the operative distal end of the occlusion clearing device is positioned within the coupler.
Figure 5B:
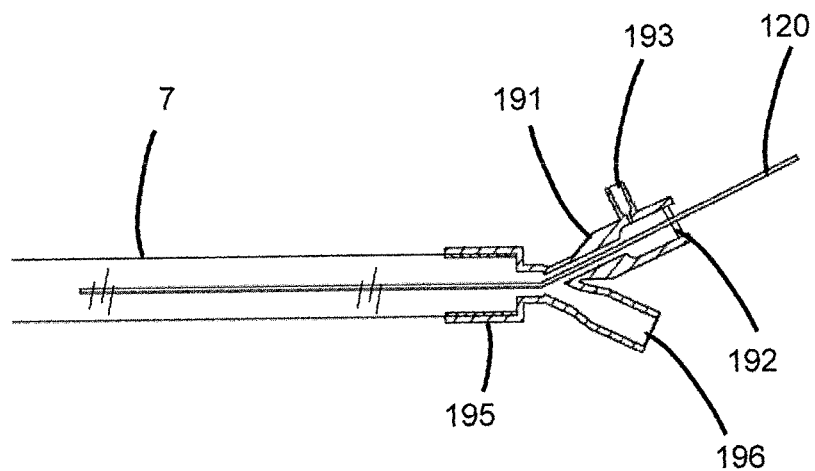
FIG. 5B is a partial cross-section of a coupler connected to an endotracheal tube, in which the operative distal end of the occlusion clearing device is inserted into the tube through the coupler.

As shown in FIGS. 5A and 5B, the occlusion clearing device 100 further includes a coupler 190 at the distal end 130 of the clearing stem 120 that provides a connection point for access to the tube 7 having occlusive material to be cleared, such as an ETT. The coupler 190 includes a clearing stem connector 191 having a chamber 194 therein into which the distal end 130 of the clearing stem is passed. The protective sleeve 138 may attach to the clearing stem connector 191 to protect the clearing stem 120 outside of the coupler 190. The coupler 190 also includes a tube connector 195 that attaches to the tube 7. The connection between the tube 7 and tube connector 195 is selectively reversible, such that the device 100 can be attached for use and then removed when clearing is complete. Attachment of the tube 7 and tube connector 195 can be by any suitable means that provides a fluidically tight seal that is selectively reversible. For example, the tube connector 195 may snap on to the tube 7, or may have threading to attach to the tube 7 in a screw-type fashion. The tube connector 195 is in fluid communication with the chamber 194 within the clearing stem connector 191, such that the clearing stem 120 can be moved between the clearing stem connector 191 and the tube connector 195 for accessing the tube 7 for clearing.

In at least one preferred embodiment, the coupler 190 further includes a diaphragm 192 that creates a fluidic seal around the clearing stem 120 when it is positioned inside the coupler 190. For instance, the diaphragm 192 may be located in the clearing stem connector 191, such that the clearing stem 120 must pass through the diaphragm 192 in order to enter the coupler 190, and specifically the chamber 194. The diaphragm 192 seals off the coupler 190, forming a closed system between the tube 7 and the clearing stem 120 during use. Also, in some embodiments, the coupler 190 may also include additional port(s), such as a ventilator port 196 that attaches to the ventilator system on which a patient may be established. Accordingly, when the ventilator system is connected to the ventilator port 196 and the tube 7 is connected to the tube connector 195, the diaphragm 192 creates a seal around the clearing stem 120, forming a closed system such that the patient can continue to be mechanically ventilated through the ventilator port 196 without any air leaks during the occlusion removal process. In other embodiments, however, the occlusion clearing device 100 may be used in an open system in which the patient is not on a ventilator system, or the ventilator system is temporarily suspended for occlusion clearing.

In use, the clearing stem 120 is positioned into the chamber 194 of the clearing stem connector 191, and the tube 7 is connected to the tube connector 195, as depicted in FIG. 5A. The clinician or user then moves the clearing stem 120 through the coupler 190 and into the tube 7, as shown in FIG. 5B, until the distal end of the clearing stem 120 is in proximity to the occlusive material to be cleared (as in FIG. 2). The occlusive material is removed from the tube 7, as shown in FIG. 2, and the clearing stem 120 is withdrawn from the tube 7, returning again to the coupler 190 as seen in FIG. 5A. Aspiration and irrigation may occur at any time during this process, including when the clearing stem 120 is being advanced into the tube 7 and as it is withdrawn from the tube 7. The clearing stem 120 may be moved in and out of the tube 7 by grasping the clearing stem 120 through the protective sleeve 138 and inching it forward or back, or it may be moved by pushing on the handset 150 at the proximal end 135 of the clearing stem 120. The coupler 190 may also be held steady with one hand if desired.

In some embodiments, the coupler 190 may also include a lavage port 193 on the clearing stem connector 191, as shown in FIGS. 5A and 5B. The lavage port 193 allows the user to clean or flush the distal end of the clearing stem 120 after use or between insertions. Accordingly, the lavage port 193 is in fluid communication with the chamber 194 therein. Lavage fluid, such as saline or other biologically suitable wash fluid, may be introduced into the lavage port 193 to remove occlusive material or other matter the clearing stem 120 may have picked up from the tube 7. This lavage fluid may then be aspirated through the aspiration lumen 122 of the clearing stem to remove it from the coupler 190.

As shown throughout FIGS. 1 and 6-8, the occlusion clearing device 100 also includes a handset 150 at the proximal end 135 of the clearing stem 120. The handset 150 is designed to be held in a single hand of the user for positioning and use of the occlusion clearing device 100. Accordingly, the handset 150 includes a body 151 that is gripped by the user, and houses various other components for actuating the device 100. For instance, the handset 150 provides the user the ability to control the aspiration flow 123 and the irrigation flow 128 with one hand, explained in detail below.

Figure 6:
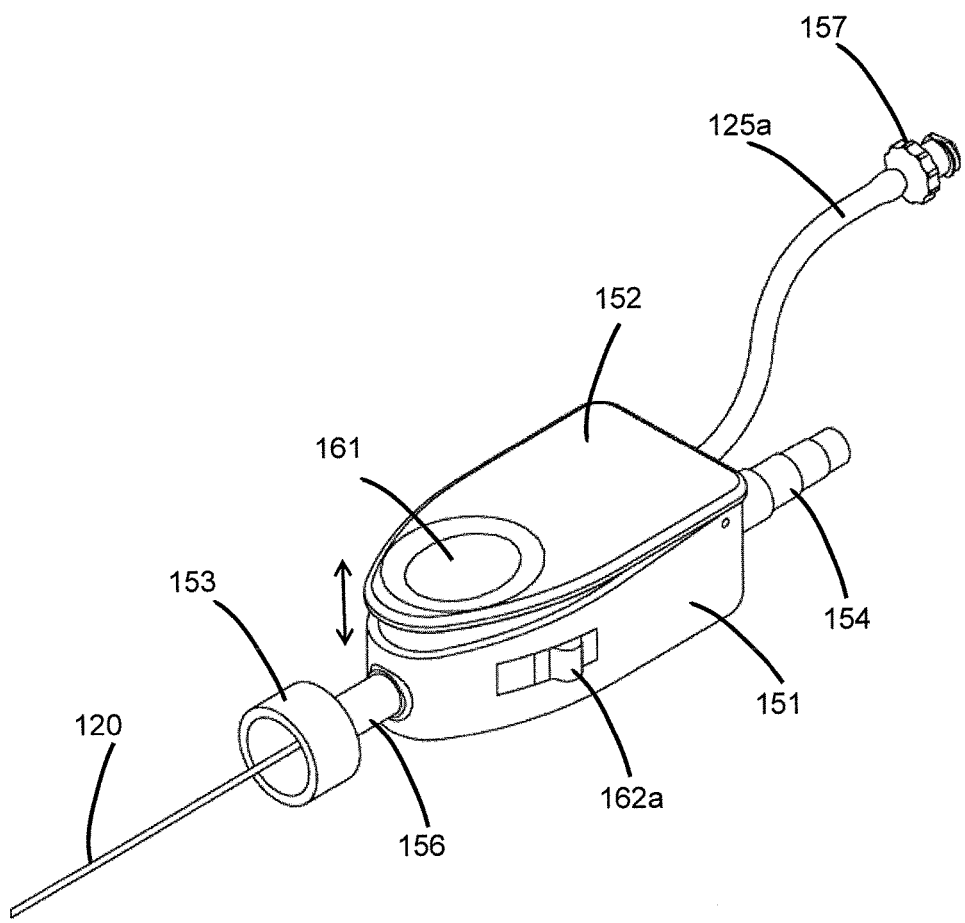
FIG. 6 is a perspective view of one embodiment of the handset at the proximal end of the clearing stem.

As illustrated in FIG. 6, the handset 150 is located at the proximal end of the clearing stem 120. The clearing stem 120 connects to the handset 150 through an adaptor 153. The adaptor 153 may connect directly or indirectly to the body 151 of the handset 150. The adaptor 153 also provides a connection point for the protective sleeve 138 (not shown) at the proximal end of the device 100, thus protecting the proximal end of the clearing stem 120.

Figure 8:
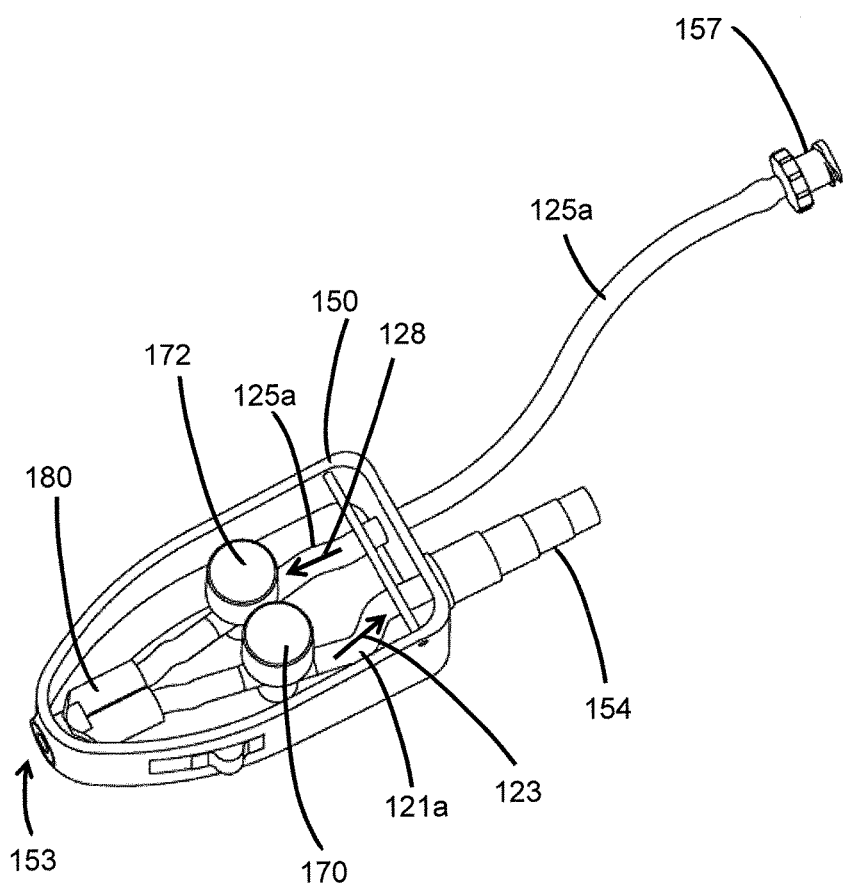
FIG. 8 is a partial cutaway of one embodiment of the handset showing the interior components of the handset.

As depicted in FIG. 8, the handset 150 includes an aspiration port 154 that connects to an aspiration source (not shown) such as a vacuum pump or other suitable source of suction. The handset 150 further includes aspiration tubing 121a disposed through at least a portion of the body 151 of the handset 150 and connecting the aspiration port 154 to the aspiration lumen 122 of the clearing stem 120 as it joins to the handset 150 through the adaptor, as shown in FIG. 6. The aspiration tubing 121a is in fluid communication with both the aspiration lumen 122 of the clearing stem 120 and the aspiration port 154 such that suction drawn at the source is communicated through the aspiration port 154, through the tubing 121a, and through the aspiration lumen 122 to the distal tip 131 of the clearing stem 120 to draw occlusive material 5 into the clearing aspiration lumen 122 for removal.

Similarly, as seen in FIG. 8, the handset 150 also includes an irrigation port 157 that connects to a source of irrigant (not shown), such as saline or other inert fluid. The handset 150 further includes irrigation tubing 125a disposed through at least a portion of the body 151 of the handset 150 and connecting the irrigation port 157 to the irrigation lumen 126 of the clearing stem 120. The irrigation tubing 125a is in fluid communication with the irrigation port 157 and the irrigation lumen 126 so that irrigant provided from the source (not shown) to the irrigation port 157 is moved through the irrigation tubing 125a and through the irrigation lumen 126 to the distal end 130 of the clearing stem 120, where it exits into the aspiration lumen 122 and mixes with occlusive material 5 therein to lubricate it for removal.

In some embodiments, the aspiration port 154 and irrigation port 157 connect directly to the body 151 of the handset. In other embodiments, as in FIG. 7D, the aspiration port 154 and irrigation port 157 may be spaced apart from the body 151 of the handset, and connect indirectly through aspiration tubing 121a and irrigation tubing 125a, respectively. Accordingly, at least a portion of aspiration tubing 121a and irrigation tubing 125a is positioned within the body 151 of the handset 150 and connects the aspiration port 154 and irrigation port 157 to the appropriate lumens 122, 126 of the clearing stem 120, and at least a portion of the aspiration tubing 121a and irrigation tubing 125a may be positioned or extend beyond the body 151 of the handset 150 for joining to distanced aspiration port 154 and irrigation port 157. Either or both of the aspiration port 154 and irrigation port 157 may be spaced apart from the body 151 of the handset 150.

Figure 7A:
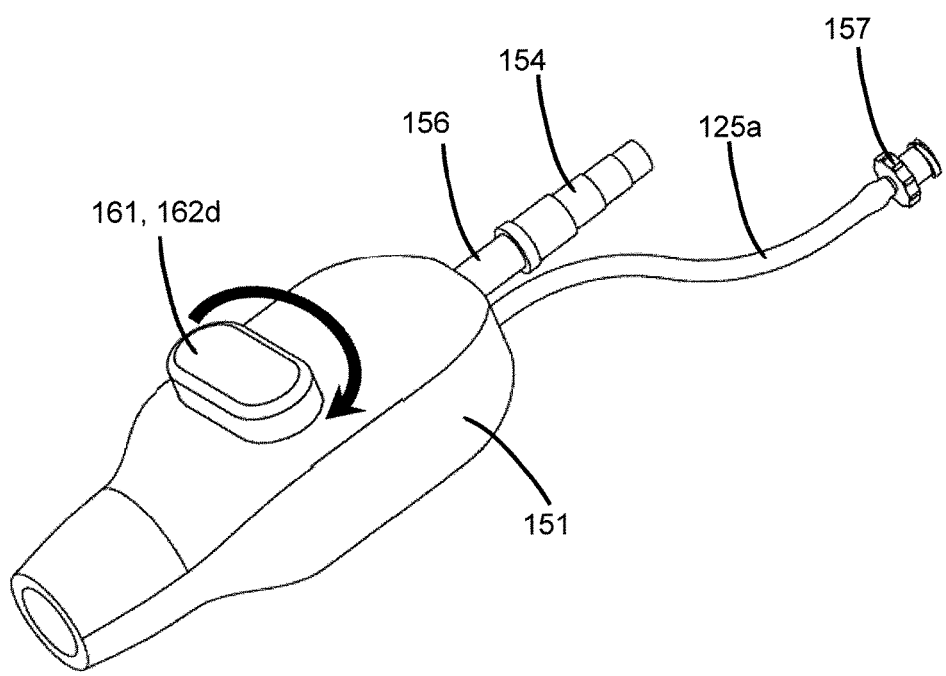
FIG. 7A is a perspective view of another embodiment of the handset.

The handset 150 may also include a viewing window 156 which coincides with a portion of the clearing stem 120 and/or aspiration tubing 121a and permits a user to see and visually monitor the occlusive material 5 as it is aspirated through the device 100. The viewing window 156 may be located anywhere along the clearing stem 120 or aspiration tubing 121a. For instance, in some embodiments, the viewing window 156 is located on the distal side of the handset 150, as shown in FIG. 6. In other embodiments, the viewing window 156 is located proximally of the handset 150 along aspiration tubing 121a, as shown in FIG. 7A. The viewing window 156 may be a portion of tubing, a window set into tubing, or may be an entire segment of tubing. In a preferred embodiment, the viewing window 156 is transparent to allow visual perception of occlusive material 5 and irrigant 127 as it is aspirated through and out of the device 100. For instance, the amount, color and consistency of the occlusive material 5, and whether any blood is also present, may be visually monitored using the viewing window 156.

Figure 9:
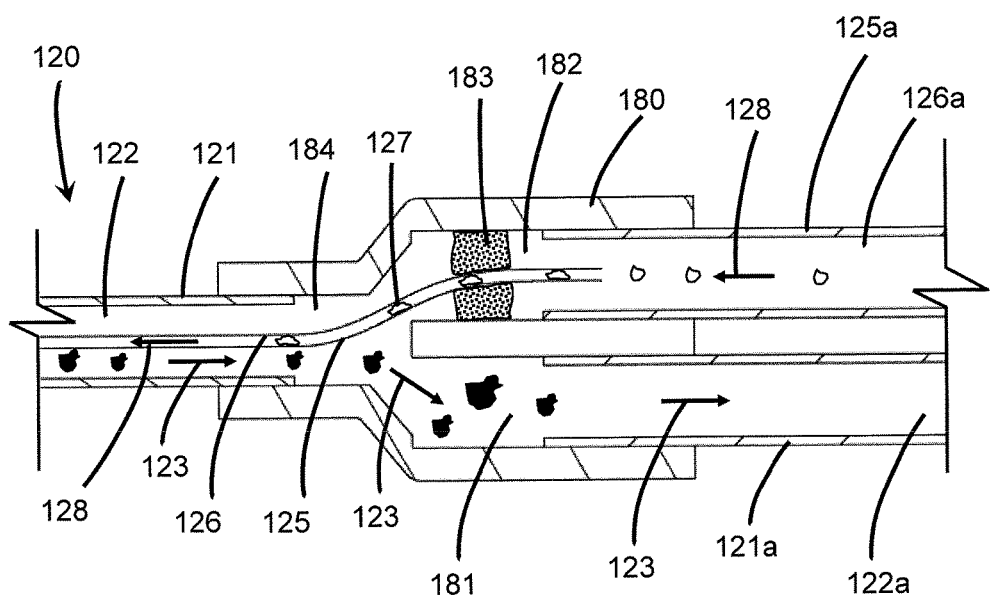
FIG. 9 is a cross-sectional view of one embodiment of the tubing junction in the handset.

The handset 150 also includes a tubing junction 180, as shown in FIGS. 8 and 9. The tubing junction 180 provides a way of combining the irrigation tubing 125a and aspiration tubing 121a in order to get the irrigation conduit 125 inside the aspiration lumen 122 in the clearing stem 120. In other words, the tubing junction 180 joins the proximal portions of the irrigation conduit 125 and aspiration conduit 121 from the clearing stem 120 with their respective distal tubings 125a and 121a in a way that enables separate irrigation and aspiration through a single combined clearing stem 120.

With particular reference to FIG. 9, the tubing junction 180 includes a first passage 181 that receives the aspiration tubing 121a in the handset 150. This first passage 181 is therefore in fluid communication with the aspiration tubing lumen 122a such that aspirated materials can move from the first passage 181 into the aspiration tubing 121a in the direction of aspiration flow 123. The tubing junction 180 also includes a second passage 182 that receives the irrigation tubing 125a in the handset 150. The second passage 182 is in fluid communication with the irrigation tubing lumen 126a, and therefore also with irrigant moving in the direction of irrigation flow 128. The tubing junction 180 further includes a third passage 184 that receives the aspiration conduit 121 and irrigation conduit 125 of the clearing stem 120.

In the embodiment of FIG. 9, the aspiration conduit 121 begins in the third passage 184 of the tubing junction 180, but the irrigation conduit 125 extends into the second passage 182. Irrigant 127 from the irrigation tubing 125a in the second passage 182 enters the irrigation conduit 125 in the second passage 182, and continues in the direction of irrigation flow 128 on into the clearing stem. Since the aspiration conduit 121 of the clearing stem only begins in the third passage 184, the irrigation conduit 125 is able to enter the aspiration lumen 122 in the third passage 184. In some embodiments, as in FIG. 9, the irrigation conduit 125 extends into the second passage 182, but is separate from the irrigation tubing 125a that may also be located in the second passage 182. In other embodiments, the irrigation conduit 125 and tubing 125a may join together, such as in the second passage 182 of the tubing junction 180. For instance, at least one of the irrigation tubing 125a or conduit 125 may taper to a common diameter shared between them, so that irrigant 127 pushed from the irrigation tubing 125a into the conduit 125 is directed into the irrigation conduit 125. These are but a few examples. Other embodiments may contemplate other ways of directing the irrigant 127 into the irrigation conduit 125 of the clearing stem 120.

Additionally, a seal 183 is provided in the tubing junction 180, such as in the second passage 182, third passage 184, or the space there between to create a fluid tight or hermetic barrier around the irrigation conduit 125 or tubing 125a within the tubing junction 180. For instance, the seal 183 may be provided in the second passage 182 around the irrigation conduit 125, as depicted in FIG. 9. The seal 183 creates a fluid communication between the aspiration lumen 122 from the clearing stem 120, the third passage 184 and first passage 181 of the tubing junction 180, and the aspiration tubing lumen 122a for aspiration. The seal 183 functions to exclude the irrigant 127 from this aspiration fluid communication. The seal 183 may be any material suitable for creating a fluid tight barrier, such as adhesive, gel, or other similar material. Further, it should be appreciated that although the embodiment of FIG. 9 shows the aspiration conduit 121 and tubing 121a as separate, in at least one other embodiment, the aspiration conduit 121 and tubing 121a may join or merge at some point in the tubing junction 180. In still other embodiments, the aspiration conduit 121 and tubing 121a may be the same, and the irrigation conduit 125 may penetrate or pass through the wall of the aspiration conduit 121, in which case the seal 183 would be formed around the irrigation conduit 125 at this point.

Figure 10A:
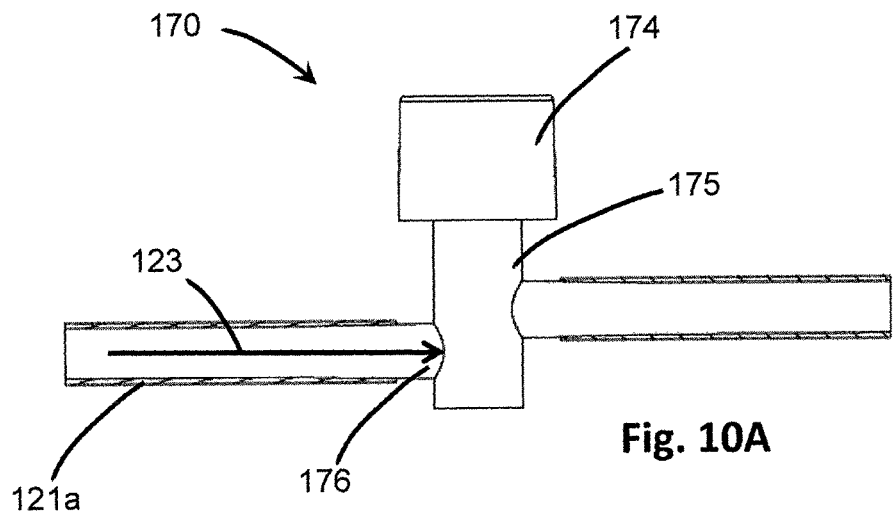
FIG. 10A is a schematic elevation view of one embodiment of the aspiration valve in the default position (closed).
Figure 10B:
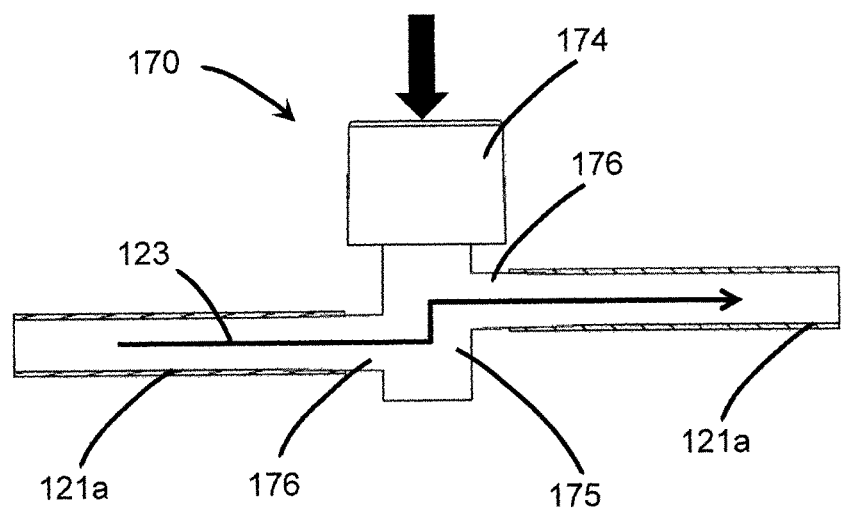
FIG. 10B is a schematic elevation view of the aspiration valve of FIG. 10A in the open position.

As shown in FIGS. 8 and 10A-10B, the handset 150 also includes valves that control each of the aspiration 123 and irrigation 128 flow. Specifically, a first valve 170 is interposed in the aspiration tubing 121a that connects the aspiration port 154 to the aspiration conduit 121 of the clearing stem 120. A second valve 172 is interposed in the irrigation tubing 125a that connects the irrigation port 157 to the irrigation conduit 125 of the clearing stem 120. The valves 170, 172 may be opened or closed to turn the aspiration 123 and irrigation 128 flow on or off, respectively. For instance, the valves 170, 172 may each have a valve top 174, a body 175, and at least one but preferably more than one arm 176, as shown in FIGS. 10A and 10B. The valve top 174 may be raised or lowered to change the valve 170, 172 between open and closed positions. Additionally, the valves 170, 172 may be any type of valve suitable for opening and closing a fluid flow path, such as but not limited to membrane valves and spring valves. As used herein, "fluid" may mean liquid, gas, combinations thereof, and may further include particulates dispersed therein, such as occlusive material 5.

For instance, in at least one embodiment, the valves 170, 172 are membrane valves that are closed when the valve top 174 is in the raised position, as in FIG. 10A, and open when the valve top 174 is lowered or depressed, as in FIG. 10B. Here, the first valve 170 is shown for illustrative purposes, but it should be understood that the second valve 172 may work in a similar fashion. For instance, the aspiration tubing 121a connects to each arm 176 of the first valve 170 such that the first vale 170 is interposed in the fluid flow path of aspiration 123. When the first valve 170 is closed, as in FIG. 10A, the aspiration flow 123 is halted at the body 175 of the first valve 170 and not permitted to pass. Aspiration is prevented from flowing through the handset 150. When the valve top 174 is lowered, as in FIG. 10B, the membrane valve that is the first valve 170 opens, permitting aspiration flow 123 through the valve body 175, into the opposing arm 176, and on into the aspiration tubing 121a on the other side of the first valve 170. Accordingly, aspiration flow 123 is permitted through the handset 150. The example of membrane valves are illustrated here, but it should be appreciated that other types of valves, such as spring valves, may operate in the reverse manner (where the valve is open when the valve top 174 is raised and closed when the valve top 174 is lowered). Various types and operations of valve are contemplated here.

The handset 150 may further include an actuator 161 located on the handset 150, such as on the body 151, that can be pressed, moved, or otherwise activated to engage and/or disengage the first and second valves 170, 172 to move them between operative and inoperative positions. In at least one embodiment, the actuator 161 is a button that is activated by rotation, as in FIG. 7A, or by pressing, as in FIGS. 7B and 7C. In other embodiments, the actuator 161 may be a portion of or the entire top surface 152 of the handset 150, as in FIGS. 6 and 7D-7E. In such embodiments, the top surface 152 may be movably connected to the body 151, such as by a hinge connection or other suitable mechanism. When the actuator 161 portion is pressed, the entire top surface 152 may pivot down, as indicated by the directional arrow in FIG. 6. When not engaged, the top surface 152 of the handset 150 may return to a raised position. These are just a few illustrative examples of the form and operation of the actuator 161, and are not intended to be limiting. For all of these examples, the actuator 161 may be activated or acted on by the hand of the user holding the handset 150, such as by pressing with the heel or edge of the hand or with a finger. Accordingly, the handset 150 may be both held and operated single-handedly by a user.

When activated, the actuator 161 engages the first and second valves 170, 172 within the handset 150 to open or close the valve. For instance, the actuator 161 pressing down on the valve tops 174 of the first and second valves 170, 172 will open or close the valves, depending on the type of valve it is. In at least one embodiment, the valves 170, 172 can thus be opened or closed simultaneously; although in other embodiments it is contemplated they may be operated independently of one another. Moreover, in some embodiments it is contemplated that partial opening or closing of the valves 170, 172 may be possible by engaging the actuator 161 variably or by degrees.

The handset 150 may also include a lock 162 that retains the actuator 161 in a particular position, and as a result also maintains the first and second valves 170, 172 in a corresponding position. For example, the lock 162 may keep the actuator 161 in a depressed or rotated position, which in turn keeps the first and second valves 170, 172 in the corresponding open or closed position (or partially opened or closed position, depending on the embodiment). Accordingly, a user may select the desired position for the actuator 161 and then lock it in place, thereby keeping the aspiration and irrigation either one or off. The user therefore does not have to continually hold down the actuator 161, but may set it and then turn their attention to the distal end of the device 100 or the viewing window 156 to monitor the occlusion clearing process. The lock 162 is also selectively releasable to permit the actuator 161 to move to another position when desired.

Figure 7B:
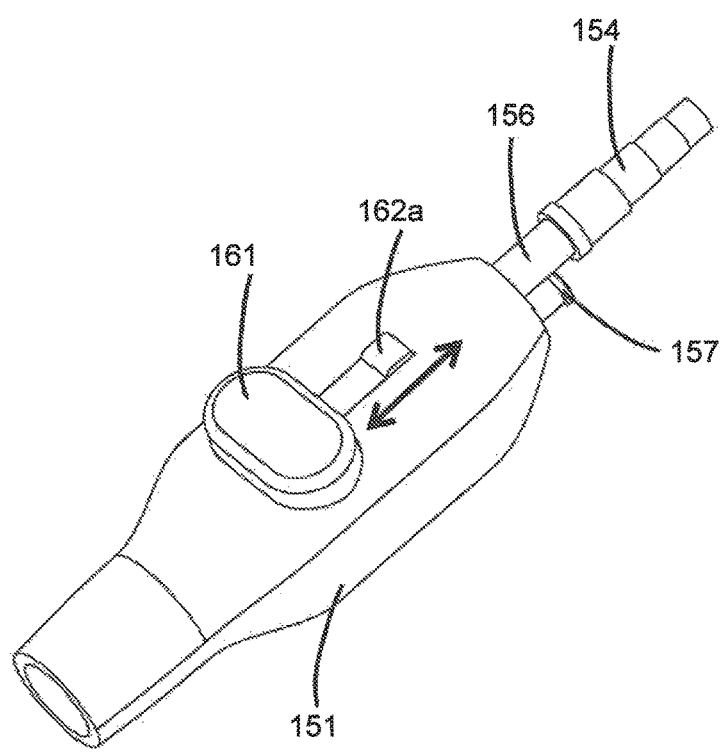
FIG. 7B is a perspective view of a third embodiment of the handset.
Figure 7C:
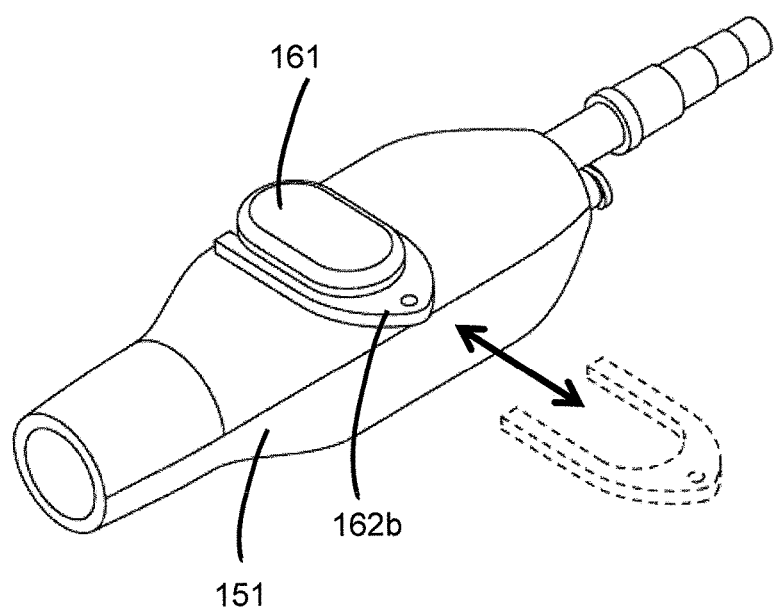
FIG. 7C is a perspective view of a fourth embodiment of the handset.
Figure 7D:
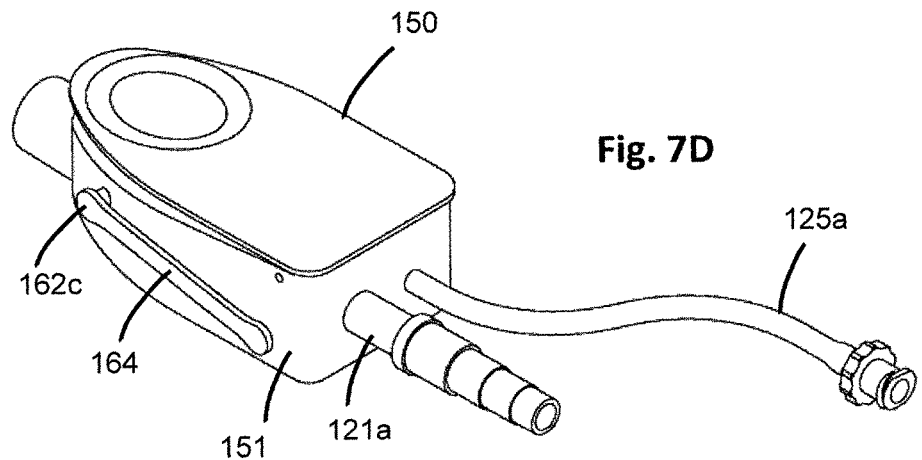
FIG. 7D and FIG. 7E are perspective views of a fifth embodiment of the handset.
Figure 7E:
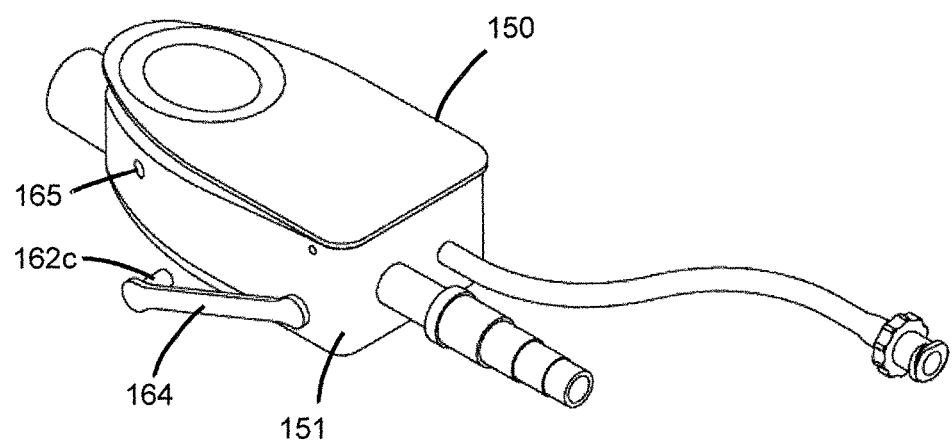

Various types of locks 162 are contemplated. For instance, in at least one embodiment as shown in FIGS. 6 and 7B, the lock 162a may be a slide lock that moves along a track between positions. In one position, the lock 162a may engage the actuator 161 and keep it in restricted engagement in a particular setting, such as up or down. In another position along the slide track, the lock 162a disengages from the actuator 161, which is then free to move to a different position. The lock and unlock positions of the lock 162a may be anywhere along the track as permits engagement and disengagement of the actuator 161. In at least one other embodiment, as depicted in FIG. 7A, the actuator 161 may itself be a lock 162d, such that the actuator 161 may be pressed to activate and rotated to lock in position, or may be rotated to both activate and lock at the same time. In other embodiments, as in FIG. 7C, the lock 162b may be a plate or other substantially planar device that may slidingly engage at least part of the actuator 161 to retain it in position. For instance, the lock 162b may be inserted around or under at least a portion of the actuator 161 when it is raised, as indicated by the directional arrow, so as to prevent it from being pressed down. In this case, the lock 162b may prevent the actuator 161 from being depressed, keeping the valves 170, 172 either open or closed depending on the corresponding position. In still other embodiments, as in FIG. 7D, the lock 162c may be a pin that is inserted into an aperture 165 in the body 151 of the handset 150 to engage the actuator 161. The lock 162c may be selectively removed from the aperture 165 to release the actuator 161, as in FIG. 7E. Accordingly, the lock 162c may be attached to a mount 164 or other structure that movably connects the lock 162c to the handset 150. As shown in FIG. 7E, the mount 164 may pivot or swing about a fixed point so as to move the lock 162c into and out of alignment with the aperture 165 for engaging or disengaging the actuator 161, respectively.

It should also be evident that the various types of locks 162a, 162b, 162c may be configured to work with different types of actuators 161. For instance, a slide lock 162a is illustrated for use with both a hinge type actuator (as in FIG. 6) and a button type actuator 161 (as in FIG. 7B).

Figure 11:
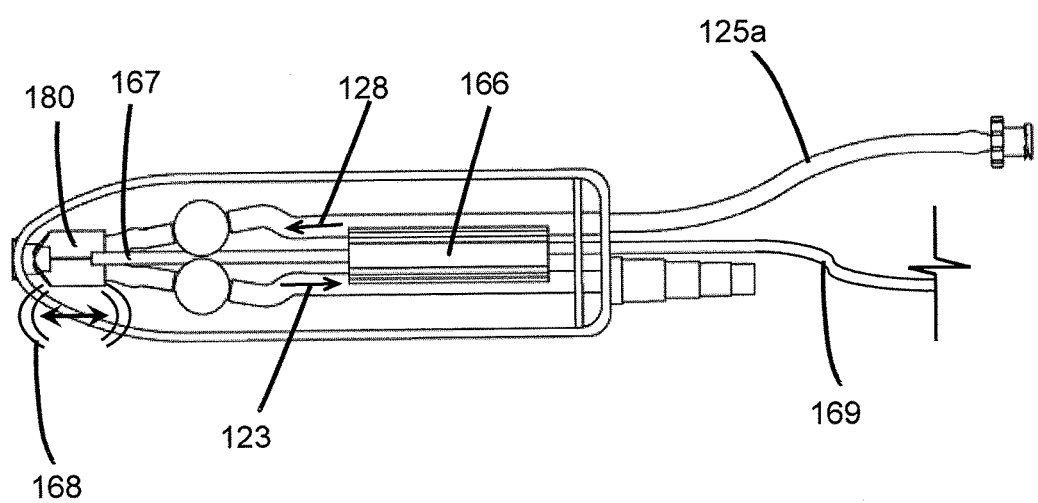
FIG. 11 is a partial cutaway of another embodiment of the handset including a motor. Like reference numerals refer to like parts throughout the several views of the drawings.

The occlusion clearing device 100 may be used with only aspiration and irrigation. In some embodiments, however, reciprocating motion may also be applied to the clearing stem 120 to assist the distal tip 131 in contacting the occlusive material 5 in the tube 7 to be cleared, and in keeping the occlusive material 5 moving through the aspiration lumen 122 of the clearing stem 120 for removal and maintain patency of the clearing stem 120. Therefore, in some embodiments, as in FIG. 11, the handset 150 may also include a motor 160 that generates reciprocating or oscillating motion. As used herein, "reciprocating" and "oscillating" may be used interchangeably to refer to motion that is back and forth in an axial direction. A shaft 167 connects to the motor 160 and transmits the reciprocating motion to the clearing stem 120, such that the clearing stem 120 is gently moved back and forth by the reciprocating motion 168. For instance, the shaft 167 may connect the motor 160 to the tubing junction 180, so as to provide the reciprocating motion 168 to the tubing junction 180, which in turn conveys the motion 168 to the clearing stem 120 attached to and extending from the opposite side of the tubing junction 180. The shaft 167 is therefore made of a rigid material, such as polymer or metal having a hardness sufficient to maintain its structure and avoid bending upon the application of reciprocating motion from the motor 166. The motor 166 may be driven by any suitable power source, such as DC power from a wall-driven power supply connected by a power cord 169, or by battery, or both.

The motor 166 may be any suitable motor capable of generating gentle reciprocating motion, such as, but not limited to, voice coil motors (VCM); DC motors; piezoelectric transducers, including amplified piezoelectric actuator (APA) motors such as those disclosed in U.S. Pat. No. 6,465,936 (Knowles, et al.), whose entire disclosure is incorporated by reference herein; piezoelectric actuators; active polymer compound actuators; solenoid motors; pneumatic motors; magnetorestrictive transducers; and electrorestrictive transducers.

For instance, in some embodiments the motor 166 may be a voice coil motor (VCM) as are commercially available. For instance, the VCM may include a displaceable motor shaft with magnets mounted thereto and coil windings wound around the VCM body. When activated, an electric current is applied through the coil windings, creating a magnetic field inside the coil windings. The non-uniform magnetic field at the ends exerts a force on the magnets on the shaft. Alternating the current alternates the direction of the magnetic field gradients and results in a reciprocating motion of the motor shaft with respect to the VCM body. The magnitude of the force is determined by the magnetic flux density, which is proportional to the number of turns per length of the coil, current magnitude, cross-sectional area of the coil, as well as the strength of the permanent magnets. Springs in the VCM absorb the energy associated with abrupt changes in the direction of the inertial force of the magnets and VCM body when actuated. By way of example only, the spring constant of the springs can range from 0.5-5 lb/in, and more preferably 1.5-2.5 lb/in. The relative positions of the coil windings and magnets can be reversed, such that the coil windings are wound directly around the motor shaft and the magnets are positioned around the VCM body and thus do not interfere with the motor shaft's reciprocation.

Alternatively, the VCM may be a dual coil motor or actuator. Instead of using magnets, two coil windings are used wherein one coil is wound directly around the motor shaft and a second or outer coil is wound around the first or inner coil but without interfering with shaft displacement. Each coil is supplied with respective alternating current sources which generate respective electromagnetic fields that also generate a reciprocating motion of the motor shaft. The inner coil may conduct direct current DC while the outer coil conducts alternating current AC. Alternatively, the inner coil may conduct alternating current AC while the outer coil conducts direct current DC, or both the inner coil and the outer coil may conduct alternating current AC. The VCM may also include a countermass or counterbalance which is driven at an opposite phase (e.g., 180° phase lag) for cancelling some or all of the vibration caused by the motor. This avoids "chatter" from the parts and therefore does not irritate the operator or patient.

In some embodiments, the motor 166 may be a DC or DC brushless motor for creating reciprocating displacement via a scotch yoke or similar mechanism. When activated, the DC motor causes a rotating crank to drive the scotch yoke slider and the scotch yoke shaft in reciprocating motion. An adapter transmits the scotch yoke motion to the scotch yoke shaft. In other embodiments, the motor 166 is an amplified piezoelectric actuator (APA) that creates reciprocating displacement in the lower range, preferably 0.1 to 2.0 mm. One or more APA motors can be used in series to increase displacement. Reciprocating motion is created by APA actuator expansion and contraction. In still other embodiments, a Langevin transducer can be used for the motor 166. A Langevin transducer comprises a plurality of piezoelectric elements arranged to cause a horn to vibrate to produce the reciprocating motion. A power source provides the proper activation energy. Lateral displacement caused by overtones produced from the horn vibrating may be minimized by compressing the piezoelectric elements. Accordingly, a standing wave is generated, which propagates to the clearing stem. In further embodiments, the motor 166 is a solenoid motor. The solenoid is pulsed during activation such that during the pulse, a solenoid shaft is driven in one direction and when the pulse is terminated, a return spring restores the solenoid shaft to the opposite direction. This action is repeated at the operative frequencies. In still other embodiments, the motor 166 may be a pneumatic motor that has a shaft which receives pneumatic pulses from a pneumatic pulse generator via an air supply. A pneumatic motor diaphragm distributes the pneumatic pulse evenly to the pneumatic motor shaft, thereby maintaining its alignment, while at the same time providing a tightly-sealed motor configuration. The pneumatic pulse causes the pneumatic motor shaft to be driven in one direction while compressing a return spring. Once the pneumatic pulse is terminated, the return spring restores the pneumatic motor shaft to the opposite direction. This action is repeated at operative frequencies.

Since many modifications, variations and changes in detail can be made to the described preferred embodiments, it is intended that all matters in the foregoing description and shown in the accompanying drawings be interpreted as illustrative and not in a limiting sense. Thus, the scope of the invention should be determined by the appended claims and their legal equivalents. Now that the invention has been described,

What is claimed is:

1. A device for in situ clearing of occlusive material, comprising:
    an aspiration conduit having at least one opening at an operative distal end, said aspiration conduit defining an aspiration lumen therein;
    an irrigation conduit disposed within and parallel to said aspiration lumen and terminating within said aspiration lumen a preselected distance from said at least one opening, said irrigation conduit defining an irrigation lumen therein: and
    a handset having:
        (i) an aspiration port;
        (ii) aspiration tubing in fluid communication between said aspiration port and said aspiration lumen;
        (iii) an irrigation port; and
        (iv) irrigation tubing in fluid communication between said irrigation port with said irrigation lumen.

2. The device as recited in claim 1, wherein said irrigation conduit is separate from said aspiration conduit.

3. The device as recited in claim 1, wherein at least a portion of said irrigation conduit is attached to said aspiration conduit.

4. The device as recited in claim 3, wherein at least a portion of said irrigation conduit and said aspiration conduit are integrally formed.

5. The device as recited in claim 1, wherein said operative distal end of said aspiration conduit has a distal tip made of a different material than said aspiration conduit.

6. The device as recited in claim 5, wherein said distal tip is more flexible than said aspiration conduit.

7. The device as recited in claim 1, wherein said at least one opening is located at a terminal end of said aspiration conduit.

8. The device as recited in claim 7, wherein said at least one opening is located a preselected distance from said terminal end of said aspiration conduit.

9. The device as recited in claim 1, further comprising a first valve interposed in fluid communication in said aspiration tubing, and a second valve interposed in fluid communication in said irrigation tubing.

10. The device as recited in claim 9, further comprising an actuator simultaneously actuating said first and second valves.

11. The device as recited in claim 10, further comprising a lock selectively retaining said actuator in at least one position.

12. The device as recited in claim 11, wherein said lock is at least one of a slide, pin, and plate.

13. The device as recited in claim 1, further comprising a tubing junction having:
    (i) a first passage in fluid communication with said aspiration tubing;
    (ii) a second passage in fluid communication with said irrigation tubing; and
    (iii) a third passage in fluid communication with said first and second passages.

14. The device as recited in claim 13, wherein said tubing junction further includes a seal around at least one of said irrigation conduit and said irrigation tubing in at least one of said second and third passages.

15. The device as recited in claim 13, wherein said handset further comprises a motor generating reciprocating motion, and a shaft mechanically connecting said motor and said tubing junction.

16. The device as recited in claim 1, wherein said handset further comprises a motor generating reciprocating motion, and a shaft mechanically interconnecting said motor and at least one of said aspiration conduit and said irrigation conduit.

17. The device as recited in claim 16, wherein said motor is at least one of a voice coil motor, a piezoelectric motor, a Langevin transducer, a DC motor, a solenoid motor, and a pneumatic motor.

18. The device as recited in claim 1, wherein said aspiration conduit and said irrigation conduit collectively define a clearing stem, and further comprising a coupler located at said operative distal end of said clearing stem, said coupler including:
    (i) a clearing stem connector defining a chamber therein, said operative distal end of said clearing stem disposed within said chamber;

(ii) a tube connector in fluid communication with said chamber, said operative distal end of said clearing stem movable from said chamber to said tube connector.

19. The device as recited in claim 18, wherein said coupler further comprises a lavage port in said clearing stem connector in fluid communication with said chamber, providing lavage fluid to clean said operative distal end of said clearing stem.

20. The device as recited in claim 18, wherein said coupler further comprises a ventilator port in fluid communication with said tube connector, providing ventilator access to said tube connector.

21. The device as recited in claim 20, wherein said coupler further comprises a diaphragm creating a fluidic seal around said clearing stem.

22. The device as recited in claim 1, wherein said aspiration conduit and said irrigation conduit collectively define a clearing stem; and further comprising a protective sleeve covering at least a portion of said clearing stem.

23. A system for in situ clearing of occlusive material, comprising:
a clearing stem having:
(i) an operative distal end;
(ii) an aspiration conduit defining an aspiration lumen therein, providing aspiration from said operative distal end, and having at least one opening at said operative distal end;
(iii) an irrigation conduit positioned interior to and terminating within said aspiration lumen, said irrigation conduit defining an irrigation lumen therein;
a handset having:
(iv) an aspiration port;
(v) aspiration tubing fluidically connecting said aspiration port with said aspiration lumen;
(vi) an irrigation port; and
(vii) irrigation tubing fluidically connecting said irrigation port with said irrigation lumen;
an aspiration source in fluid communication with said aspiration lumen, said aspiration source providing negative pressure for aspiration from said operative distal end to said aspiration source; and
an irrigation source in fluid communication with said irrigation lumen, said irrigation source providing irrigant to said irrigation conduit such that said irrigant flows from said irrigation source, through said irrigation lumen, exits said irrigation conduit and is substantially aspirated away from said operative distal end of said irrigation conduit through said aspiration lumen in the direction of said aspiration source.

24. The system as recited in claim 23, wherein said irrigation conduit is separate from said aspiration conduit.

25. The system as recited in claim 23, wherein at least a portion of said irrigation conduit is attached to said aspiration conduit.

26. The system as recited in claim 25, wherein at least a portion of said irrigation conduit and said aspiration conduit are integrally formed.

27. The system as recited in claim 23, wherein said operative distal end of said aspiration conduit terminates in a distal tip made of a different material than said aspiration conduit.

28. The system as recited in claim 27, wherein said distal tip is more flexible than said aspiration conduit.

29. The system as recited in claim 23, wherein said at least one opening is located at a terminal end of said aspiration conduit.

30. The system as recited in claim 29, wherein said at least one opening is located a preselected distance from said terminal end of said aspiration conduit.

31. The system as recited in claim 23, further comprising a first valve controlling aspiration flow through at least one of said aspiration tubing and said aspiration conduit, and a second valve controlling irrigation controlling irrigation flow through at least one of said irrigation tubing and said irrigation conduit.

32. The system as recited in claim 25, further comprising an actuator simultaneously actuating said first and second valves.

33. The system as recited in claim 32, further comprising a lock selectively retaining said actuator in position so as to maintain said first and second valves in at least one of an open or closed position.

34. The system as recited in claim 33, wherein said lock is at least one of a slide, pin, and plate.

35. The system as recited in claim 23, further comprising a tubing junction having:
(i) a first passage receiving said aspiration tubing;
(ii) a second passage receiving said irrigation tubing; and
(iii) a third passage joining said aspiration tubing with said aspiration conduit and said irrigation tubing with said irrigation conduit, such that said clearing stem extends from said tubing junction with said irrigation conduit disposed within said aspiration lumen.

36. The system as recited in claim 35, wherein said tubing junction further includes a seal in at least one of said second and third passages creating a fluidic barrier around said irrigation tubing within said tubing junction.

37. The system as recited in claim 35, wherein said handset further comprises a motor generating reciprocating motion, and a shaft connecting said motor and said tubing junction and transmitting said reciprocating motion to said clearing stem through said tubing junction.

38. The system as recited in claim 23, wherein said handset further comprises a motor generating reciprocating motion, and a shaft extending from said motor and transmitting said reciprocating motion to said clearing stem.

39. The system as recited in claim 38, wherein said motor is at least one of a voice coil motor, a piezoelectric motor, a Langevin transducer, a DC motor, a solenoid motor, and a pneumatic motor.

40. The system as recited in claim 23, further comprising a coupler located at said operative distal end of said clearing stem, said coupler including:
(i) a clearing stem connector having a chamber receiving said operative distal end of said clearing stem;
(ii) a tube connector in fluid communication with said chamber and selectively attachable to a tube having occlusive material to be removed, said operative distal end of said clearing stem is movable into said tube through said tube connector.

41. The system as recited in claim 40, wherein said coupler further comprises a lavage port in said clearing stem connector providing lavage fluid to clean said distal end of said clearing stem.

42. The system as recited in claim 40, wherein said coupler further comprises a ventilator port in fluid communication with said tube connector providing ventilator access to said tube connector and said tube.

43. The system as recited in claim 42, wherein said coupler further comprises a diaphragm creating a fluidic seal around said clearing stem.

44. The system as recited in claim 23, further comprising a protective sleeve covering at least a portion of said clearing stem.

\* \* \* \* \*